US006654627B2

(12) United States Patent
Petrenko (10) Patent No.: US 6,654,627 B2
(45) Date of Patent: Nov. 25, 2003

(54) METHOD AND DEVICE FOR RECORDING POLARIZED ELECTROMAGNETIC RADIATION OF INACTIVATED STRAIN OF PATHOGENIC MICROORGANISMS ONTO A CRYSTAL, METHOD AND DEVICE FOR CHANGING ACTIVITY OF STRAIN OF PATHOGENIC MICROORGANISMS, METHOD FOR ELIMINATING STRAIN OF PATHOGENIC MICROORGANISMS FROM HUMAN OR ANIMAL ORGANISM

(76) Inventor: Sergei Ivanovich Petrenko, Zhukova,d.16,kv.50, Nizhny Novgorod (RU), 603137

( * ) Notice: Subject to any disclaimer, the term of this patent is extended or adjusted under 35 U.S.C. 154(b) by 296 days.

(21) Appl. No.: 09/920,045

(22) Filed: Aug. 1, 2001

(65) Prior Publication Data

US 2002/0065538 A1 May 30, 2002

(30) Foreign Application Priority Data

Nov. 30, 2000 (RU) ........................................ 2000128449

(51) Int. Cl.[7] .............................. A61N 5/00; A61B 6/00
(52) U.S. Cl. ................................ 600/407; 600/9; 607/1
(58) Field of Search ........................ 600/407, 9; 607/88, 607/94, 1; 128/898

(56) References Cited

U.S. PATENT DOCUMENTS

| 3,859,527 A | * | 1/1975 | Luckey ........................ 250/327 |
| 5,366,435 A | * | 11/1994 | Jacobson ........................ 600/13 |
| 5,489,590 A | * | 2/1996 | Gulliya et al. ............ 514/224.8 |
| 5,792,184 A | | 8/1998 | Zhou et al. |
| 5,830,140 A | * | 11/1998 | Dillinger et al. ............. 600/407 |
| 5,968,527 A | * | 10/1999 | Litovitz ........................ 424/400 |
| 6,217,604 B1 | * | 4/2001 | Azure et al. .................... 607/88 |
| 6,458,071 B1 | * | 10/2002 | Jacobson ........................... 600/9 |
| 2003/0028070 A1 | * | 2/2003 | Jacobson ........................... 600/9 |

FOREIGN PATENT DOCUMENTS

| EP | 0 686 406 A1 | * | 12/1995 | ............. A61N/1/00 |
| EP | 1 205 766 A1 | * | 5/2002 | ............. G01T/1/11 |
| RU | 2055604 | | 3/1996 | |

OTHER PUBLICATIONS

"Luminescene and Defects of Ionic Crystals", Radiation Physics, vol. 5, Zinatne, Riga, 1967.
Publications About the Inventions Registered in the State Invention Register of the USSR, "Phenomenon of intracellular distanced electromagnetic interactions in a system of two tissue cultures".
N.L. Lupichev, "Electropuncture diagnosis, homepathy and phenomenon of distance action",.
Fritz Albert Pope, "Some features of biophotons and their interpretation in Terms of Coherent States", available at www.datadiwan.de.

* cited by examiner

Primary Examiner—Shawna J Shaw
(74) Attorney, Agent, or Firm—Baker Botts LLP (57) ABSTRACT

The present invention relates to a method for recording polarized electromagnetic radiation of an inactivated strain of pathogenic microorganisms onto a crystal, a method and a device for changing the activity of a strain of pathogenic microorganisms, a method for eliminating a strain of pathogenic microorganisms in a human or animal organism. The invention may be used for inactivation and subsequent elimination of pathogenic and conditionally pathogenic microorganisms in a human or animal organism.

17 Claims, 7 Drawing Sheets

METHOD AND DEVICE FOR RECORDING POLARIZED ELECTROMAGNETIC RADIATION OF INACTIVATED STRAIN OF PATHOGENIC MICROORGANISMS ONTO A CRYSTAL, METHOD AND DEVICE FOR CHANGING ACTIVITY OF STRAIN OF PATHOGENIC MICROORGANISMS, METHOD FOR ELIMINATING STRAIN OF PATHOGENIC MICROORGANISMS FROM HUMAN OR ANIMAL ORGANISM

FIELD OF THE INVENTION

The present invention relates to medical engineering, and more exactly to a method and device for recording polarized electromagnetic radiation of an inactivated strain of pathogenic microorganisms onto a crystal, a method and a device for changing the activity of a strain of pathogenic microorganisms, a method for eliminating a strain of pathogenic microorganisms from a human or animal organism.

The invention may be used for inactivation and subsequent elimination of pathogenic and conditionally pathogenic microorganisms from a human or animal organism.

BACKGROUND OF THE INVENTION

The discovery "Phenomenon of intracellular distanced electromagnetic interactions in a system of two tissue cultures" (registered in the USSR State Register of Discoveries of Feb. 15, 1966, diploma 122, authors V. P. Kaznacheev, S. P. Shurim, L. P. Mikhailova) was placed at the base of the present invention.

An earlier unknown phenomenon of distant intracellular electromagnetic interactions between two identical tissue cultures during the action of factors on one of them, the factors being of biological, chemical or physical nature, with a characteristic reaction of another culture in the form of a "mirror" cytopathic effect, which determines the cellular system as a detector of the modulation features of electromagnetic radiation, was experimentally established.

Thus, a new information channel in biological systems was detected, and an approach to evaluation of quantum phenomenon in the mechanisms of functioning of a genetic cell program and processes of encoding information in specialized cellular systems was also experimentally developed.

The possibility appeared for investigation of means for acting on pathological processes via correction of interference occurring in the photon channel of information transmission. It is presumed that this may be related to selection of chemical compounds, converting the initial light flux of a cell into monochromatic radiation. The possibility of using a new principle for treatment of a number of diseases appeared. New methods for diagnosis of the states and prognosis of the behavior of biological objects were developed on the basis of a study of the modulation characteristics of electromagnetic radiation of biosystems.

A device for generating electromagnetic radiation for controlling and improving the state of live organisms is also known (see, for example, U.S. Pat. No. 5,792,184, 1998), the device comprising a source of energy and a generator of biofrequency spectrum, comprising an energy converter and one of the following elements or compounds thereof: Co, Cu, Mo, Li, Be, Mg, Al, Si, K, Ca, Ti, V, Cr, Mn, Fe, Ni, Zn, Ge, Sr, Zr, Nb, Ta, Hf, Se, Tn, W, Au and Y.

The device comprises a source of energy, an energy converter, an element ensuring generation of the biofrequency spectrum being imitated. This element is made in the form of a monomer or compounds consisting of one or several chemical elements. After excitation by the energy of transition of energetic levels, electromagnetic radiation is formed in the element in the form of a physical field of the biofrequency spectrum being imitated, which acts on live organisms. Where there is agreement with the poles of intensive absorption of the organism, a large part of the radiation energy carried by electromagnetic waves is absorbed, causing changes in the energy of molecules, atoms or electrons in live organisms, which then causes oscillation, increases biooxidation and improves the energetic state of cells, resulting in an increase of the permeability of cellular membranes.

The generator of the biofrequency spectrum being imitated comprises a substrate of non-metals or ceramic, a radiating layer applied onto the substrate and consisting of borides, nitrides, carbides, sulfides or fluorides, mixed with a liquid binder, and an energy converter in the form of a electrical heating wire disposed in the substrate and arranged at the end faces of the substrate to convert electrical energy into thermal energy.

The heat formed by the heating wire is used to excite chemical elements in the radiation layer.

This device radiates signals of a bioresonant spectrum with wavelengths in the range of from $0.2\,\mu m$ to 10 mm. The device has the following main characteristics. In the first place, the device provides for generation of a very wide spectrum of electromagnetic radiation, which covers the visible light band, the near and far IR band, the millimeter wave band and the centimeter wave band, i.e. completely covers the band of frequencies inherent to the natural radiation frequencies of the organism. In the second place, it is known that electromagnetic radiation differs in respect to intensity in different bands of the spectrum, wherein more than 90% of the radiated energy is in the visual light band of the near, middle and far IR bands. Wherein the ultralongwave portion of the TR band, submillimeter and millimeter bands occupy a very wide band, but only a very small amount of the radiated energy is contained therein.

In the process of operation, the energy converter converts the electromagnetic electrical energy into thermal energy and maintains a predetermined temperature of the components, ensuring the generation of electromagnetic oscillations in the range of from 0.2 to 10000 $\mu m$.

It should be noted that even though this device ensures generation of electromagnetic radiation in the range of radiation of live organisms of from $0.2\,\mu m$ to 10 mm, it is not capable, in the first place, of effectively changing the conformation of the transmembrane molecules located on the plasmatic membrane of pathogenic and conditionally pathogenic microbes, since thermal radiation of a component of the substrate is unpolarized or weakly-polarized and, in the second place, of selectively acting on cells of the organism, for example, to reduce the activity of pathogenic microbes in the organism without changing the activity of the organism's own cells and the cells of the commensal microflora of this organism.

A method of changing the activity of biological cells which is based on the phenomenon of intracellular distanced action in a system of two identical cultures is known (see, for example, N. L. Lupichev "Electropuncture diagnosis, homeopathy and phenomenon of distance action," pp. 31–45, Moscow, 1995).

The method consists in that a cell culture (strain of a microorganism) was placed in two test tubes between which contact was maintained via glass substrates. One of the test tubes with a strain of microorganisms was subjected to the action of an extreme agent, which was either a virus of classical bird plague or mercury bichloride or ultraviolet radiation. Wherein, conversion of the strain of the microorganism from an active state to an inactivated state was implemented.

Then the test tube with the inactivated strain of microorganisms was placed adjacent to the test tube in which the strain was in the active state. Twelve thousand experiments were carried out. As a result it was found that under the action of the bioelectromagnetic radiation of the inactivated strains, the active strains went into the inactivated state.

Using this method the conversion of a strain from an active state into an inactivated state may only be carried out in test tubes. However, the use of the indicated method for treatment of patients is not possible in view of the fact that it is necessary to have an active pathogenic strain of microorganisms available, but this is not always possible. Furthermore, there is a certain danger when working with active strains which are in a test tube. In order to inactivate them, an extreme agent, which is also dangerous for humans, is necessary.

Some of the aspects of the discovery made by Alexander Gurich are disclosed in the publication by Fritz Albert Pope—"Some Properties of Biophotons and Their Interpretation under Conditions of Coherent States" in a magazine of the International Institute of Biophysics, Germany, 1999. Gurvich called the emission of photons from live cells "mitogenetic radiation," which was not accepted by this contemporaries, but at the present time has been put at the base of many works.

The energy of activation encompasses the whole electromagnetic spectrum of radiation from radio waves, microwaves, infrared radiation up to the visual and even ultraviolet radiation. And there is only one carrier for the transfer of energy to millions of reactions per second and to each cell—this is unheated photons. A coherent photon field is the source of such photons. Therefore a weak flow of photons from a biological object, which is well known at present and includes the whole spectrum of radiation from ultraviolet to infrared, is called with biophotons and may be quite sufficient to carry out the role of controlling the biochemistry and biology of a live organism.

The thermoluminescence, or more exactly—thermostimulated luminescence, phenomenon is also known (see, for example, "Thermoluminescence of Lithium Fluoride," pp. 212–215 in the monograph "Radiation Physics," v. 5, "Luminescence and Defects of Ionic Crystals," published by Zinatie, Riga, 1967). This phenomenon is based on absorption by the crystal of photons of the gamma band, roentgen and ultraviolet bands and the creation in the crystal of stable energetic states or coloring centers which carry information on the band and the dose of electromagnetic action. This phenomenon is widely used in thermoluminescence dosimetry. Alkali halogen crystals, for example, lithium fluoride, are used as the sensitive element.

A recording of the electromagnetic action is carried out at a constant temperature of the crystal in the range of from 70° K. to 300° K.

Reading the information recorded on the crystal is carried out by changing the temperature of the crystal in the range of from 110° K. to 800° K., wherein the spectrum of the information signal radiated by the crystal is primarily in the visual region of the spectrum from 0.3 to 0.7 $\mu$m.

These crystals makes it possible to retain the recorded information only within several weeks or months, to carry out the reading of the recorded information by changing the temperature of the crystal within the range of from 110° K. to 800° K. with the radiation spectrum within the range of from 0.3 to 0.7 $\mu$m.

A device is known for changing the activity of a biological cell (see, for example, RF patent No. 2055604, 1993), comprising a unit for action which carries out reception and transmission of electromagnetic waves and which is positioned adjacent the biological cell. The unit for action is made in the form of a single element and carries out the storage of received electromagnetic waves. A unit for changing the temperature is connected to the unit for action.

The devices makes it possible to change the activity of biological cells of one type without changing the activity of biological cells of other types as a result of the resonant interaction of electromagnetic waves of low intensity of the device and cells on its bioresonant frequency.

The device operates in the following manner. At first information is recorded in a memory on the metabolic activity of deposited cells, changed in any known manner. With the aid of the unit for changing temperature, a single element is heated. Wherein information on a changed metabolic activity of deposited cells at a bioresonant frequency is recorded in the memory. Heating is carried out with subsequent forced or natural cooling. Cooling may first be carried out, and then heating, which composes a cycle of changing the temperature of a single element.

Then a patient—a carrier of pathogenic microorganisms, the activity of which should be changed, is placed directly adjacent a single element and a temperature change cycle is carried out. Wherein, the generator radiates electromagnetic waves of low intensity at the bioresonant frequency of the cells. As a result of the radiation the metabolic activity of the cell being irradiated is set similar to that deposited with a changed metabolic activity. In order to maintain the predetermined metabolic activity of the cells being irradiated for a lengthy period of time, repeated sessions of irradiation are carried out at certain intervals of time.

The device does not provide a high degree of inactivation of pathogenic microorganisms and does not make it possible to effectively eliminate different pathogenic and conditionally pathogenic microorganisms which are in the organism of a human being or animal.

The efficiency of operation of this device rapidly falls in the process of conducting therapeutic sessions, and furthermore, the device in the process of operation constantly accumulates parasitic polarized radiation from other strains of pathogenic microorganisms which are in an active state in the live organism being irradiated.

SUMMARY OF THE INVENTION

The object at the base of the instant invention is to create a method for recording polarized electromagnetic radiation of an inactivated strain of pathogenic microorganisms, and also a device for realization of this method.

Another object at the base of the instant invention is to create a method for changing the activity of a strain of pathogenic microorganisms.

Another object at the base of the instant invention is to create a method for eliminating a strain of pathogenic microorganisms in the organism of a human or animal with the aid of a device for changing the activity of a strain of pathogenic microorganisms.

Another object at the base of the instant invention is to create a device for recording polarized electromagnetic radiation of an inactivated strain of pathogenic microorganisms.

Another object at the base of the instant invention is to create a device for changing the activity of a strain of pathogenic microorganisms, in which the presence of a unit for restoring information makes it possible via n working cycles to effect restoration of the parameters of the working radiating cell and to increase the efficiency of operation of the device and the degree of inactivation of pathogenic microorganisms, and also to efficiently eliminate different pathogenic and conditionally pathogenic microorganisms which are in the organism of a human or animals, and the presence of a unit for deleting information and a unit for storing standard information makes it possible to ensure the recording of parasitic information at an extremely low level.

The indicated object is achieved in a method for recording polarized electromagnetic radiation of an inactivated strain of pathogenic microorganisms, in that in accordance with the invention, a deposited strain of pathogenic microorganisms in a vessel is acted on by an extreme agent selected from the group consisting of ultraviolet radiation with a wavelength within the limits of from 0.1 to 0.3 $\mu$m for a period of time t of from 10 to 300 sec, viruses and toxic substances, during the action conversion of the strain of pathogenic microorganisms is effected from an active state to an inactivated state, wherein the potential on a cellular shell of the microorganism and the conformation of membrane and transmembrane molecules positioned on that shell change, the strain of inactivated pathogenic microorganisms is placed directly adjacent a means for recording and reproducing a spectrum of radiation of biological cells, at least one cycle of changing the temperature of the means for recording and reproducing a spectrum of radiation of biological cells is effected within the range of from 10° C. to 400° C. and while the temperature on said means for recording and reproducing a spectrum of radiation of biological cells is changing, polarized electromagnetic radiation with a wavelength in the range of from 3 $\mu$m to 10 mm of the inactivated strain of pathogenic microorganisms is recorded, wherein stable energetic states are formed on the means for recording and reproducing a spectrum of radiation of biological cells, by means of which states the means for recording and reproducing a spectrum of radiation of biological cells is capable of radiating similar polarized electromagnetic waves during subsequent cycles of changes of its temperature.

It is advisable that at least one crystal selected from the group consisting of silicon, germanium, diamond, gallium arsenide be used as the means for recording and reproducing a spectrum of radiation of biological cells.

It is useful that a chip containing at least two crystalline semiconductors having different types of conductance and at least one semiconductor junction be used as the means for recording and reproducing a spectrum of radiation of biological cells.

It is advantageous that simultaneously with the recording of polarized electromagnetic radiation of the strain of inactivated pathogenic microorganisms on the means for recording and reproducing a spectrum of radiation of biological cells, action be effected on the strain of pathogenic microorganisms with electromagnetic radiation in the range of from 10 Hz to $10^{14}$ Hz.

It is useful that the chance of the temperature of the means for recording and reproducing a spectrum of radiation of biological cells be effected according to a linear law.

It is also useful that the change of the temperature of the means for recording and reproducing a spectrum of radiation of biological cells be effected according to a nonlinear law.

The indicated object is also achieved in a method for changing the activity of a strain of pathogenic microorganisms, in that in accordance with the invention, a means for recording and reproducing a spectrum of radiation of biological cells is used on which polarized electromagnetic radiation of a strain of inactivated pathogenic microorganisms is recorded with the aforesaid method for recording the means for recording and reproducing a spectrum of radiation of biological cells is placed directly adjacent to the strain of pathogenic microorganisms, the activity of which it is desired be reduced, to be similar to an inactivated strain of pathogenic microorganisms, at least one cycle of changing, the temperature of the means for recording and reproducing a spectrum of radiation of biological cells is effected for from 1 msec to 1000 sec in the range of from 10° C. to 400° C., as a result of which the means for recording and reproducing a spectrum of radiation of biological cells radiates polarized electromagnetic radiation, the aforesaid polarized electromagnetic radiation of the means for recording and reproducing a spectrum of radiation of biological cells is used to irradiate a strain of pathogenic microorganisms, the strain of pathogenic microorganisms is converted from an active state to an inactivated state by the strain of pathogenic microorganisms absorbing the polarized electromagnetic radiation from the aforesaid means for recording and reproducing a spectrum of radiation of biological cells.

The stated object is achieved in that a device for recording polarized electromagnetic radiation of an inactivated strain of pathogenic microorganisms comprising a working cell disposed in a vessel with a strain of inactivated pathogenic microorganisms and having a least one means for recording and reproducing a spectrum of radiation of biological cells, and a means for changing temperature which is coupled to the means for recording and reproducing a spectrum of radiation of biological cells, a control unit connected to the means for changing temperature, in accordance with the invention comprises at least one auxiliary cell for restoring the level of polarized electromagnetic radiation of a strain of inactivated pathogenic microorganisms in the working cell, also disposed in the vessel with the strain of inactivated pathogenic microorganisms, having at least one means for recording and reproducing a spectrum of radiation of biological cells, and a means for changing temperature which is coupled to the means for recording and reproducing a spectrum of radiation of biological cells, the auxiliary cell being connected via its inputs to respectively an output of the control unit and to outputs of subsequent auxiliary cells, and via its output to an input of the working cell, wherein the working and auxiliary cells are electrically coupled by means of a wire to each other and to the strain of inactivated pathogenic microorganisms.

It is advisable that the device comprise at least one standard cell disposed in the vessel with the strain of inactivated pathogen microorganisms, serving for restoration of the level of polarized electromagnetic radiation of the strain of inactivated pathogenic microorganisms in the working cell and in the auxiliary cell, having at least one means for recording and reproducing a spectrum of radiation of biological cells and a means for changing temperature which is coupled to the means for recording and reproducing a spectrum of radiation of biological cells, and being connected respectively via its inputs to an output of the control unit and to outputs of subsequent standard cells, and via its output to an input of the working cell and to inputs of the auxiliary cells, wherein the standard cell is electrically coupled to the working cell, to the auxiliary cell and to the strain of inactivated pathogenic microorganisms by means of an electrical link.

It is useful that the device comprise a generator of electromagnetic oscillations which is mounted directly adjacent to the vessel containing the strain of inactivated pathogenic microorganisms.

It is advantageous that a chip containing at least two crystalline semiconductors having different types of conductance and at least one semiconductor junction be used as the means for recording and reproducing a spectrum of radiation of biological cells.

It is useful that at least one crystal selected from the group consisting of silicon, germanium, diamond, gallium arsenide be used as the means for recording and reproducing a spectrum of radiation of biological cells.

The indicated object is also achieved in a device for changing the activity of a strain of pathogenic microorganisms comprising a working cell having a least one means for recording and reproducing a spectrum of radiation of biological cells on which polarized electromagnetic radiation of a strain of inactivated pathogenic microorganisms is recorded, and a means for changing temperature which is coupled to the means for recording and reproducing a spectrum of radiation of biological cells, a control unit connected to the means for changing temperature, in accordance with the invention comprises at least one auxiliary cell for restoring the level of polarized electromagnetic radiation of a strain of inactivated pathogenic microorganisms in the working cell, having at least one means for recording and reproducing a spectrum of radiation of biological cells on which polarized electromagnetic radiation of a strain of inactivated pathogenic microorganisms is recorded, and a means for changing temperature which is coupled to the means for recording and reproducing a spectrum of radiation of biological cells, the auxiliary cell being connected via its inputs to respectively an output of the control unit and to outputs of subsequent auxiliary cells, and via its output to an input of the working cell.

It is advisable that the device comprise at least one standard cell serving for restoration of the level of polarized electromagnetic radiation of the strain of inactivated pathogenic microorganisms in the working cell and in the auxiliary cell, having at least one means for recording and reproducing a spectrum of radiation of biological cells on which polarized electromagnetic radiation of a strain of inactivated pathogenic microorganisms is recorded, and a means for changing temperature which is coupled to the means for recording and reproducing a spectrum of radiation of biological cells, and being connected respectively via its inputs to an output of the control unit and to outputs of subsequent standard cells, and via its output to an input of the working cell and to inputs of the auxiliary cells, a unit for deleting polarized electromagnetic radiation, an input of which is connected to an output of the control unit, an output to an input of the working cell and to an input of at least one auxiliary cell, serving to delete polarized electromagnetic radiation from strains of microorganisms which are in an active state and in an inactivated state from the working cell and at least from one auxiliary cell.

It is useful that the working cell, at least one auxiliary cell and at least one standard cell be positioned directly adjacent to each other and be coupled to each other by means of an electromagnetic link.

It is advisable that a chip containing at least two crystalline semiconductors having different types of conductance and at least one semiconductor junction be used as the means for recording and reproducing a spectrum of radiation of biological cells.

The indicated object is also achieved in a method for eliminating a strain of pathogenic microorganisms from the organism of a human being or animal, in that in accordance with the invention the device for changing the activity of a strain of pathogenic microorganisms described above is used, the device is disposed directly adjacent the patient and at least one cycle of changing the temperature of the means for recording and reproducing a spectrum of radiation of biological cells, on which polarized electromagnetic radiation of a strain of inactivated pathogenic microorganisms is recorded, is carried out, at least one cycle of irradiation of a patient is carried out with polarized electromagnetic radiation having a length of from 1 msec to 1000 sec with a frequency within the limits of from 1 to 48 sessions per day for from 3 days to 2 months.

BRIEF DESCRIPTION OF THE DRAWINGS

Further the invention will be explained by a description of the best embodiments with reference to accompanying drawings, in which:

FIGS. 8a, b show diagrams of sequences of control pulses which are fed from the control unit to the working cell and a diagram of a change of the activity of a strain of pathogenic microorganisms during their elimination from a human organism, in accordance with the invention.

DESCRIPTION OF THE PREFERRED EMBODIMENTS

A device for recording polarized electromagnetic radiation of an inactivated strain of pathogenic microorganisms comprises a working cell 1 (FIG. 1), disposed in a vessel 2 with a strain of inactivated pathogenic microorganisms.

Figure 1:
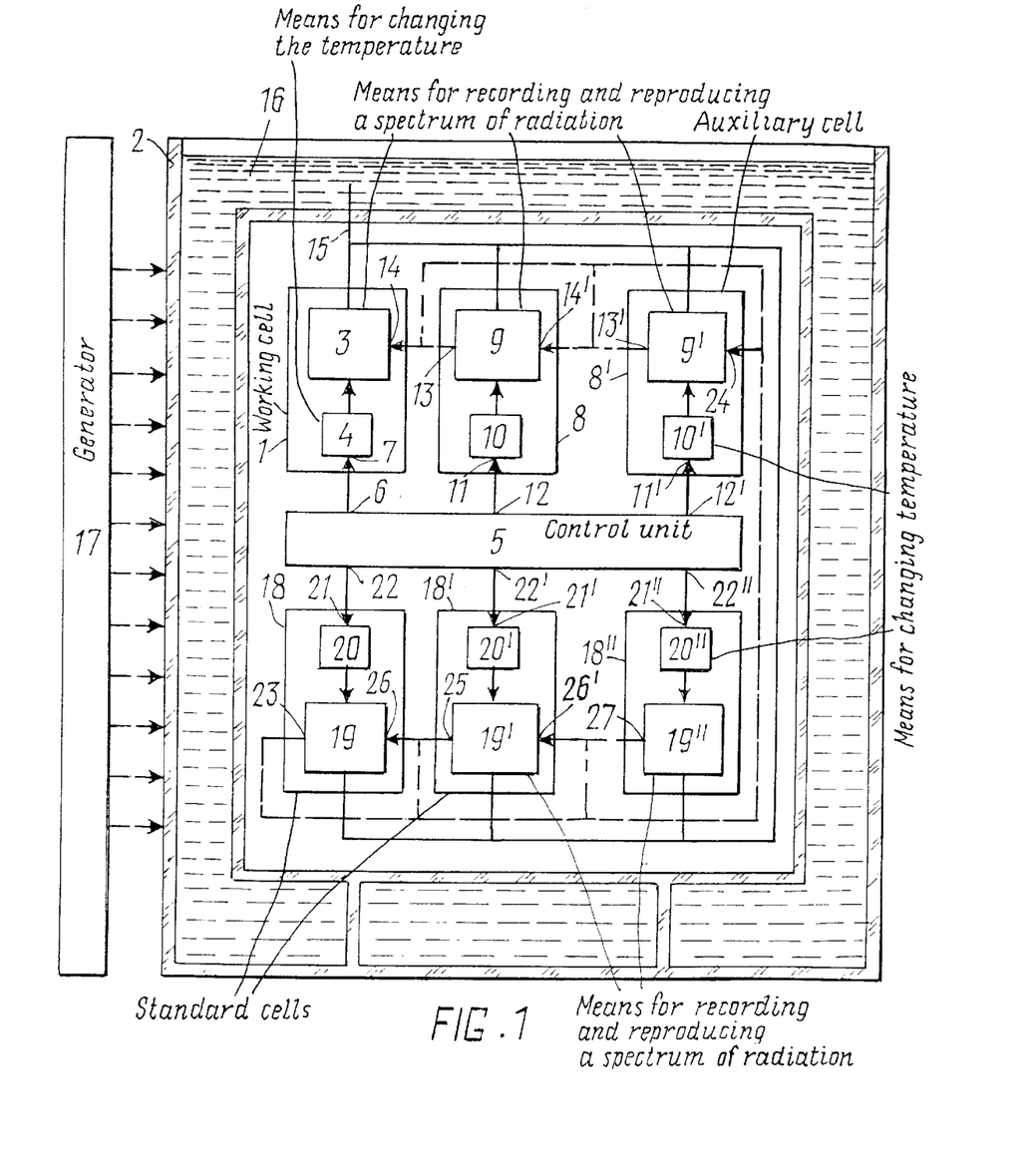
FIG. 1 shows a device for recording polarized electromagnetic radiation of an inactivated strain of pathogenic microorganisms, in accordance with the invention.

The working cell 1 has at least one means 3 for recording and reproducing a spectrum of radiation of biological cells and a means 4 for changing the temperature which is coupled to a means 3 for recording and reproducing a spectrum of radiation of biological cells.

The device also comprises a control unit 5 which is connected via its output 6 to an input 7 of the means 4 for changing temperature.

In accordance with the invention the device comprises at least one auxiliary cell 8 which serves for restoration of the level of polarized electromagnetic radiation of a strain of inactivated pathogenic microorganisms in the working cell and is also disposed in the vessel 2 with the strain of inactivated pathogenic microorganisms.

The auxiliary cell 8 has at least one means 9 for recording and reproducing a spectrum of radiation of biological cells and a means 10 for changing temperature which is electrically connected to the means 9 for recording and reproducing a spectrum of radiation of biological cells. The means 10 for changing temperature is connected via its input 11 to an output 12 of the control unit 5. Wherein the means 9 for recording and reproducing a spectrum of radiation of biological cells is connected via output 13 to an input 14 of the means 3.

FIG. 1 shows a device comprising one working cell 1 and two auxiliary cells 8, 8'. Wherein an output 13' is connected to an input 14' of the means 9 and to the input 14 of the means 3. A means 10' of the second auxiliary cell 8' is connected via input 11' to output 12' of the control unit 5.

The working cell 1 is electrically coupled by means of a wire 15 to a strain 16 of inactivated pathogenic microorganisms disposed in the vessel 2.

The device contains a generator 17 of electromagnetic oscillations, which is mounted directly adjacent the vessel 2 containing the strain 16 of inactivated pathogenic microorganisms and serves to generate a wide spectrum of electromagnetic oscillations.

The control unit 5 works in accordance with a predetermined algorithm which determines the sequence of connecting the cells. An example of the algorithm is provided below.

The device also contains at least one standard cell 18 disposed in the vessel 2. The purpose of this cell is to restore the level of polarized electromagnetic radiation of the strain of inactivated pathogenic microorganisms in the working cell 1 and in the auxiliary cells 8, 8'. In the embodiment being described the device contains three standard cells 18, 18' and 18" and means 19, 19', 19", 20, 20', 20".

The standard cell 18 has at least one means 19 for recording and reproducing a spectrum of radiation of biological cells, to which a means 20 for changing temperature is connected.

An input 21 of the means 20 is connected to an output 22 of the control unit 5. Wherein an output 23 of the means 19, which serves as an output of the standard cell 18, is connected to the input 14 of the means 3 serving as an input of the working cell 1, to an input 14' of the means 9 of the auxiliary cell 8 and to an input 24 of a means 9'.

In the aforesaid device the means 19 of the standard cell 18 is coupled via the wire 15 to the means 9 of the auxiliary cell 8, to the means 9' of the auxiliary cell 8', to the means 3 of the working cell 1 and the strain 16 of inactivated pathogenic microorganisms, and also to the means 19', 19" of the standard cells 18', 18".

In the embodiment being described an output 25 of the means 19"! for recording and reproducing a spectrum of radiation of biological cells of the standard cell 18' is connected to an input 26 of the means 19 for recording and reproducing a spectrum of radiation of biological cells of the standard cell 18, to the input 14 of the means 3 for recording and reproducing a spectrum of radiation of biological cells of the working cell 1.

An output 27 of the means 19" is connected to an input 26' of the means 19'. Inputs 21' and 21" of the means are connected to outputs 22' and 22" of the control unit 5.

In the aforesaid device a chip 28, containing at least two crystalline semiconductors having different types of conductance and at least one semiconductor junction, is used as the means 3 or 9 or 19 (FIG. 2) for recording and reproducing a spectrum of radiation of biological cells. In the embodiment being described, the chip 28 contains three crystalline semiconductors 29, 30, 31, wherein the crystalline semiconductor 29 serves as a collector, the crystalline semiconductor 30 as a base and the crystalline semiconductor 3' as an emitter. Wherein the base semiconductor 30 with respect to the collector semiconductor 29 and to the emitter semiconductor 3' 1 has different types of conductance.

Figure 2:
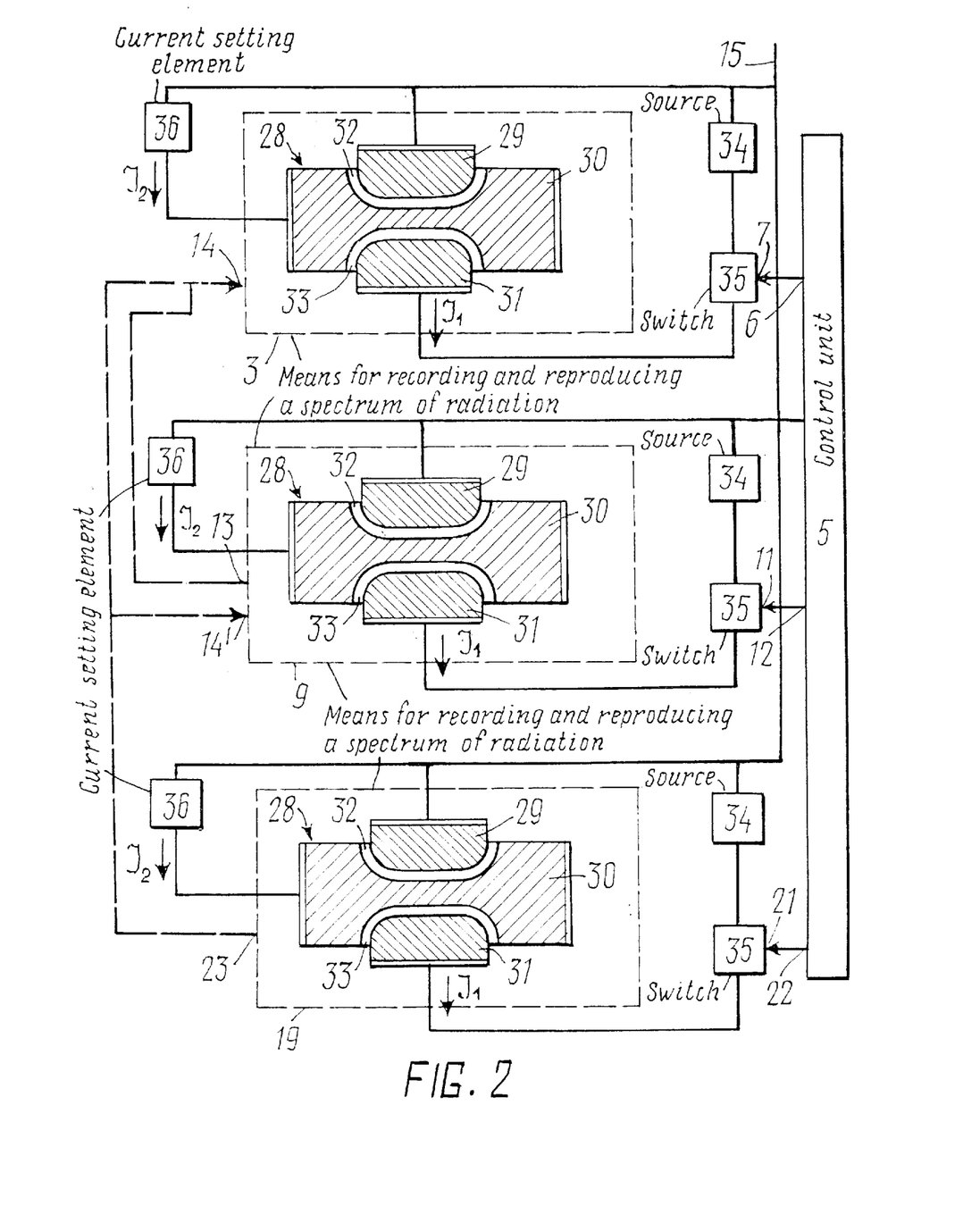
FIG. 2 shows a variant of execution of the means for recording and reproducing a spectrum of radiation of biological cells, used in a device for recording polarized electromagnetic radiation of an inactivated strain of pathogenic microorganisms, in accordance with the invention.

In the aforesaid device, collector junction 32 and emitter junction 33, which are positioned respectively between the collector and base semiconductors 29, 30 and between the base and emitter semiconductors 30, 31, are used as the means 4 or 10 or 20 for changing temperature. These semiconductors are connected to a source 34 via a switch 35. The temperature T to which the crystalline semiconductors 29, 30, 31 are heated is determined by the power P which is dissipated on the semiconductor junctions 32, 33 when current flows, and is determined by the equation $$T=f(P),$$

$$P=I_1 \times U=I_2 \times \beta \times U,$$

where: $I_1$ is the emitter current, $I_2$ is the base current, U is the voltage between the collector and emitter, $\beta$ is a transfer constant of the base current.

Using a current setting element 36 connected to the base semiconductor 30, it is possible to adjust the value of the current $I_2$ flowing through the base semiconductor 30, and consequently the temperature T to which the chip 28 is heated.

Execution of the means 3 on the base of a transistor chip is more preferable than the execution of that means on the base of a diode chip, since the former makes it possible to use the source 34 with a wider range of change of the supply voltage and to use its energy with maximum efficiency.

Crystals of silicon, germanium, diamond and gallium arsenide may be used as the crystalline semiconductor.

The method for recording polarized electromagnetic radiation of an inactivated strain of pathogenic microorganisms onto a crystal is carried out in the following manner.

At first a preparatory operation is carried out, wherein action is taken on a to deposited strain of pathogenic microorganisms which is in a test tube (not shown in FIG. 1) with an extreme agent selected from the group consisting of toxic substances or viruses or ultraviolet radiation with a wavelength within the range of from 0.1 to 0.3 μm during a period of time t within the range of from 10 to 300 seconds. During the action, a transition of the strain of pathogenic microorganisms from an active state into an inactivated state takes place, wherein the potential on the cellular shell of the microorganism and the conformation of the membrane and transmembrane molecules positioned on that shell change.

When the conformation of the membrane and transmembrane molecules changes, the polarization of the electromagnetic waves radiated therefrom changes, i.e. the membrane and transmembrane molecules of the cellular shell of an inactivated strain of pathogenic microorganisms after their irradiation with electromagnetic waves in the ultraviolet range will radiate photons of primarily one type of polarization.

Thus, the spectrum of radiation of an inactivated strain of pathogenic microorganisms after their irradiation with electromagnetic waves in the ultraviolet range will include therein a polarization component.

Therefore, an inactivated strain of pathogenic microorganisms may be presented in the form of a low-power generator of polarized radiation with a spectrum of radiation equivalent to the spectrum of radiation of membrane and transmembrane molecules of an inactivated strain of pathogenic microorganisms.

The test tube with the strain of inactivated pathogenic microorganisms is positioned directly adjacent to a means for recording and reproducing a spectrum of radiation of biological cells. In the described embodiment the strain of inactivated pathogenic microorganisms is placed in a vessel 2 (FIG. 1) in which a working cell 1 is arranged with a means 3 for recording and reproducing a spectrum of radiation of biological cells and with a means 4 for changing temperature.

Then at least one cycle of changing the temperature of the means for recording and reproducing a spectrum of radiation of biological cells in a range of from 10° C. to 400° C. is carried out, wherein the temperature may at first increase and then decrease, or vice versa, at first decrease and then increase. In the embodiment being described the temperature changes in the range of from 20° C. to 130° C.

Figure 3A:
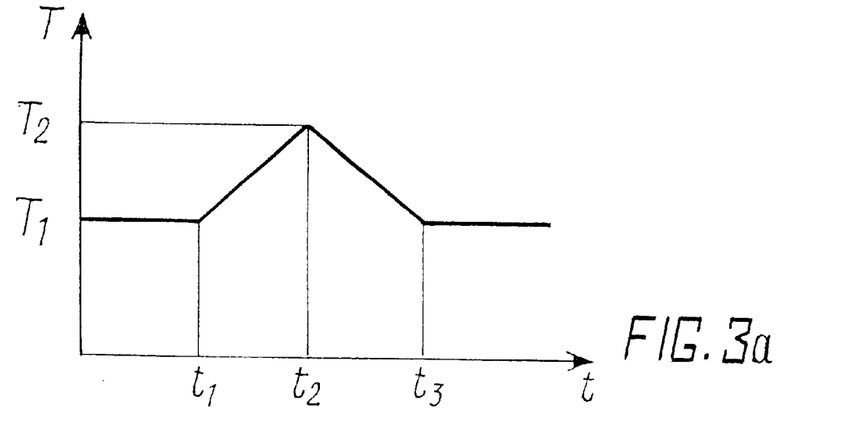
FIGS. 3a, b, c show diagrams of a change of the temperature of the means for recording and reproducing during the recording and reproducing of polarized electromagnetic radiation of an inactivated strain of pathogenic microorganisms, in accordance with the invention.
Figure 3B:
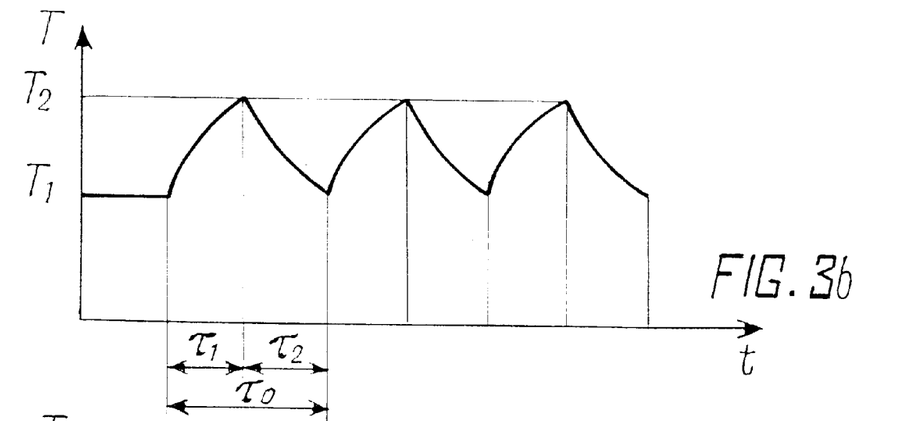
Figure 3C:
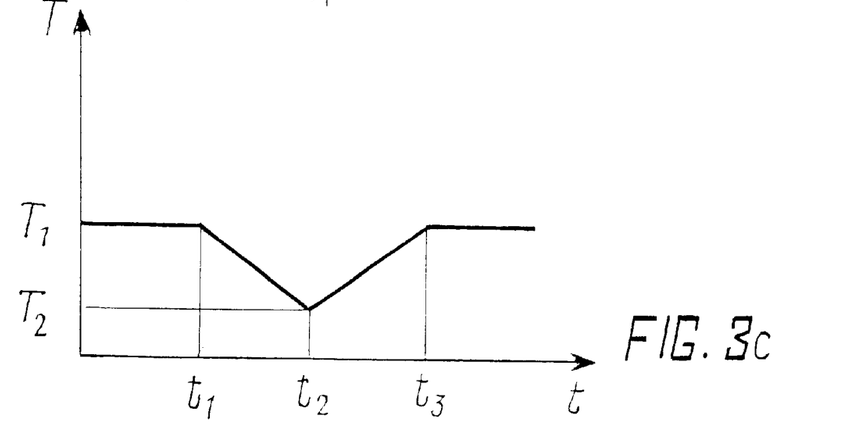

The change of the temperature of the means 3 for recording and reproducing a spectrum of radiation of biological cells is carried out in accordance with a linear law (FIG. 3a) or a nonlinear law (FIG. 3b). A variant is shown in FIG. 3a where the temperature changes according to a linear law, but at first it increases and then decreases. A variant is shown in FIG. 3c where the temperature changes according to a linear law, but at first it decreases and then increases.

While the temperature of the means 3, 9, 9', 19, 19', 19" for recording and reproducing a spectrum of radiation of biological cells is changing, a polarized electromagnetic radiation with a wavelength in the range of from 3 μm to 10 mm of an inactivated strain of pathogenic microorganisms is recorded thereon. Wherein stable energetic states are formed on the aforesaid means for recording and reproducing a spectrum of radiation of biological cells, by means of which the means 3, 9, 9', 19, 19', 19" for recording and reproducing a spectrum of radiation of biological cells will radiate polarized electromagnetic waves when their temperature changes.

The means 3, 9, 9', 19, 19'. 19" for recording and reproducing a spectrum of radiation of biological cells may be presented as retransmitters of photons which are radiated by conforming membrane and transmembrane molecules of the cellular shell of inactivated strain 16 of pathogenic microorganisms.

A chip 28 (FIG. 2) is used as the means 3, 9, 9', 19, 19', 19" for recording reproducing a spectrum of radiation of biological cells.

Simultaneously with recording polarized electromagnetic radiation of a strain of inactivated pathogenic microorganisms on the means for recording and reproducing a spectrum of radiation of biological cells, action is effected on the strain of pathogenic microorganisms with electromagnetic radiation from the generator 17 of electromagnetic oscillations, which is in the range of from 10 Hz to $10^{14}$ Hz in order to increase the intensity of radiation of the strain 16 of inactivated pathogenic microorganisms.

The block diagram of the device for changing the activity of a strain of pathogenic microorganisms is on the whole similar to the block diagram of the device for recording polarized electromagnetic radiation of an inactivated strain of pathogenic microorganisms.

The device for changing the activity of a strain of pathogenic microorganisms contains a working cell 37 (FIG. 4) disposed in a body 38.

Figure 4:
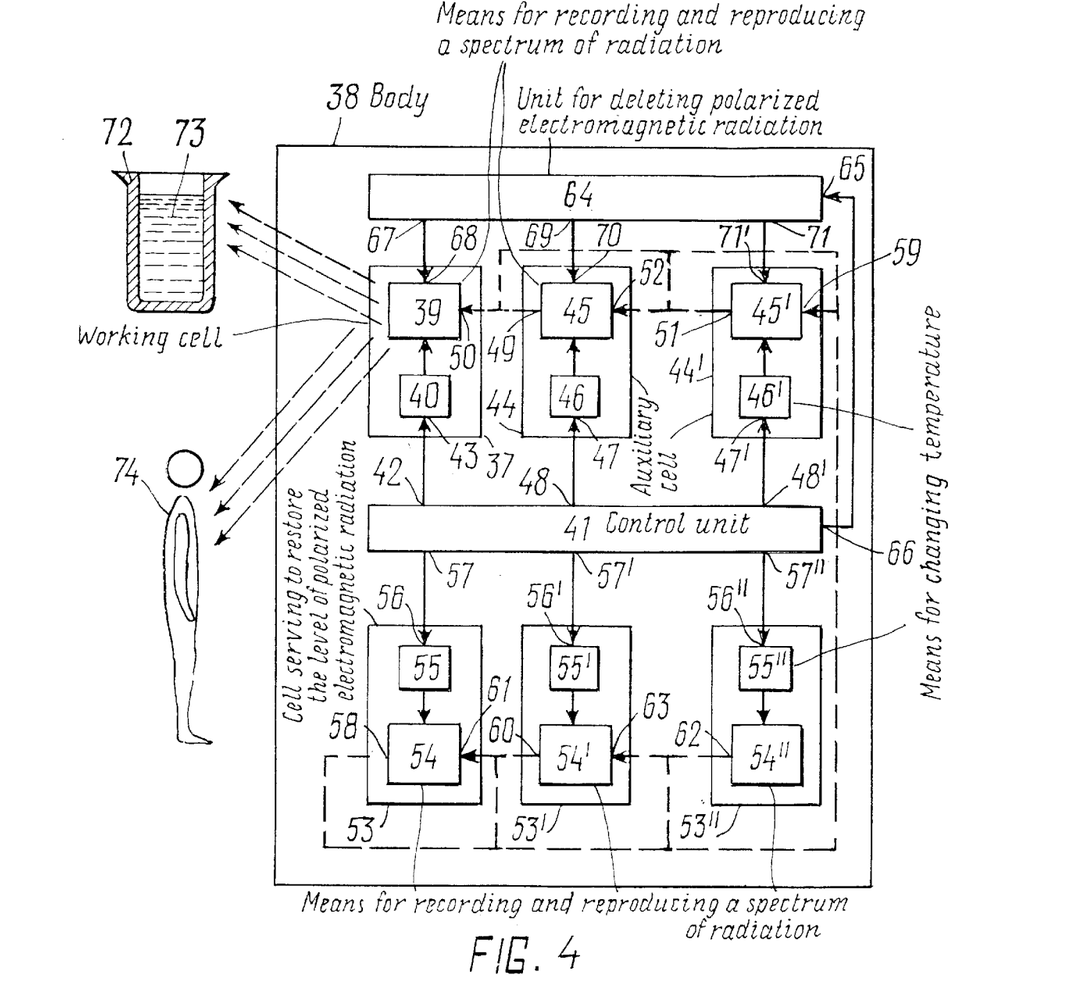
FIG. 4 shows a device for changing the activity of a strain of pathogenic microorganisms, in accordance with the invention.

The working cell 37 has at least one means 39 for recording and reproducing a spectrum of radiation of biological cells and a means 40 for changing temperature which is coupled to the means 39 for recording and reproducing a spectrum of radiation of biological cells.

The device also contains a control unit 41 which is connected at its output 42 to an input 43 of the means 40 for changing the temperature of a crystal.

In accordance with the invention the device contains at least one auxiliary cell 44 which serves for restoration of the level of polarized electromagnetic radiation of a strain of inactivated pathogenic microorganisms in a working cell and is also disposed in the body 38'.

The auxiliary cell 44 has at least one means 45 for recording and reproducing a spectrum of radiation of biological cells and a means 46 for changing temperature which is electrically coupled to the means 45 for recording and reproducing a spectrum of radiation of biological cells. The means 46 for changing temperature is connected at its input 47 to an output 48 of the control unit 41, while the output 49 of the means 45 is connected to an input 50 of the means 39 of the working cell 37.

A device is shown in FIG. 4 which contains one working cell 37 and two auxiliary cells 44 and 44'. The auxiliary cell 44' contains a means 45' for recording and reproducing a spectrum of radiation of biological cells which is electrically coupled to a means 46' for changing temperature, an input 47' of which is connected to an output 48' of the control unit 41.

An output 51 of the means 45' is connected to an input 52 of the means 45 and to the input 50 of the means 39.

The device contains at least one standard cell 53 also disposed in the body 38, the cell 53 serving to restore the level of polarized electromagnetic radiation of a strain of inactivated pathogenic microorganisms in the working cell 37 and in the auxiliary cells 44 and 44'.

The standard cell 53 has at least one means 54 for recording and reproducing a spectrum of radiation of biological cells to which a means 55 for changing temperature is connected. An input 56 of the means 55 of the standard cell 53 is connected to an output 57 of the control unit 41. Wherein an output 58 of the means 54 of the standard cell 53 is connected to the input 50 of the means 39 of the working cell 37, to the input 52 of the means 45 of the auxiliary cell 44 and to an input 59 of the means 45' of the auxiliary cell 44'.

In the variant being described, the device contains three standard cells 53, 53', 53", containing means 54, 54', 54" for recording and reproducing a spectrum of radiation of biological cells, to which the means 55, 55', 55" for changing temperature are respectively connected. Wherein, inputs 56', 56" of the means 55', 55" are connected to outputs 57', 57" of the control unit 41. An output 60 of the means 54' is connected to an input 61 of the means 54, and also to the input 50 of the means 39, to the input 52 of the means 45, and to the input 59 of the means 45'. An output 62 of the means 54" is connected to an input 63 of the means 54', to the input 61 of the means 54, and also to the input 50 of the means 39, to the input 52 of the means 45, to the input 59 of the means 45'.

The device also contains a unit 64 for deleting polarized electromagnetic radiation, an input 65 of which is connected to an output 66 of the control unit 41, while an output 67 is connected to an input 68 of the means 39 of the working cell 37, an output 69—to an input 70 of the means 45 of the auxiliary cell 44, an output 71 to an input 71' of the means 45' of the auxiliary cell 44'.

In this device the means 39, 45, 45', 54, 54', 54" are made similar to means 3, 9, 19.

In the aforesaid device a chip 28, containing at least two crystalline semiconductors having different types of conductance and at least one semiconductor junction, is used as the means 39 (FIG. 5) or 45 or 54 for recording and reproducing a spectrum of radiation of biological cells. In the embodiment being described, the chip 28 contains three crystalline semiconductors 29, 30, 31, wherein the crystalline semiconductor 29 serves as a collector, the crystalline semiconductor 30 as a base and the crystalline semiconductor 31 as an emitter. Wherein the base semiconductor 30 with respect to the collector semiconductor 29 and to the emitter semiconductor 31 has different types of conductance.

Figure 5:
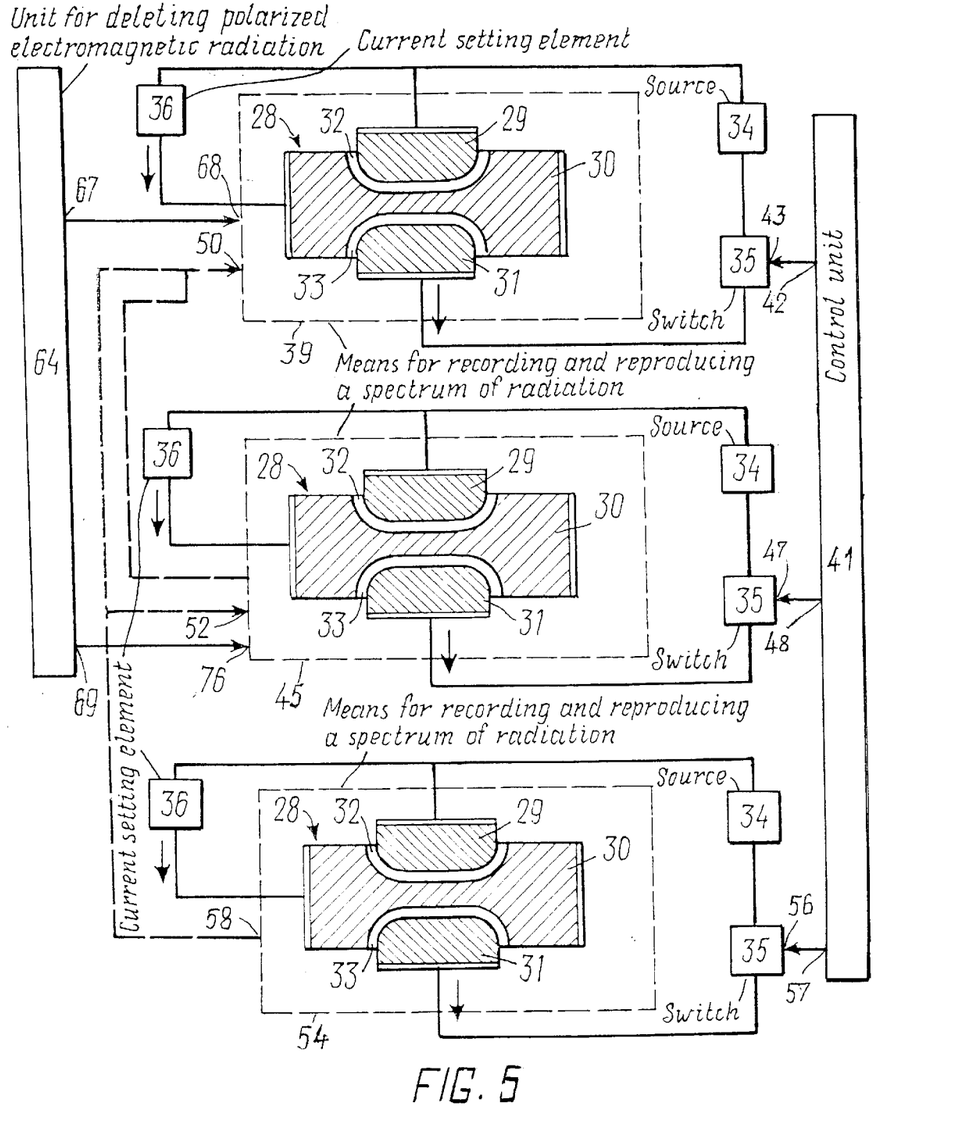
FIG. 5 shows a variant of embodiment of the means for recording and reproducing a spectrum of radiation of biological cells, which is used in the device for changing the activity of a strain of pathogenic microorganisms, in accordance with the invention.
Figure 6:
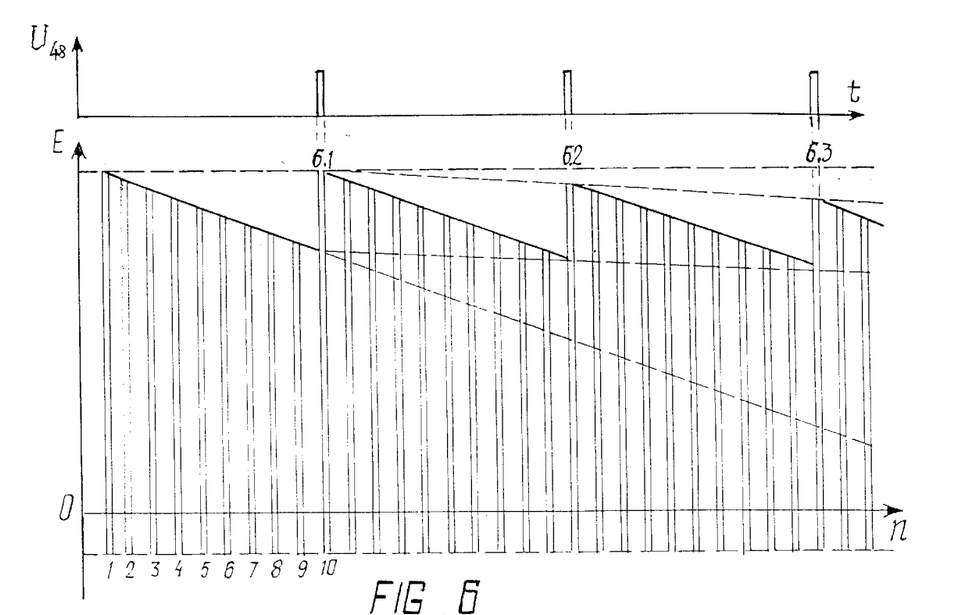
FIG. 6 shows a diagram of a change of the value of the cutoff voltage E on the plasmatic membrane of a strain of pathogenic microorganisms in relation to the number n of test tubes, in accordance with the invention.
Figure 7A:
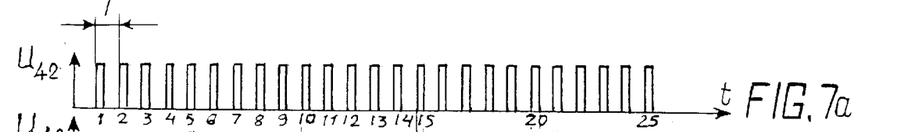
FIGS. 7a–7j show diagrams of control pulses which are fed from the control unit to the working, auxiliary and standard cells and to the generator for deleting, diagrams of changes of the level of polarized electromagnetic radiation of an inactivated strain of pathogenic microorganisms on the working, auxiliary and standard cells and diagrams of changes of parasitic polarized electromagnetic radiation on the working and auxiliary cells, in accordance with the invention.
Figures 7B, 7C:
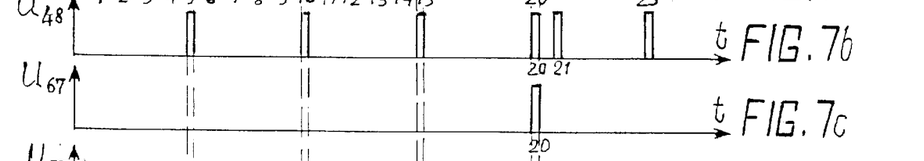
Figures 7D, 7E:
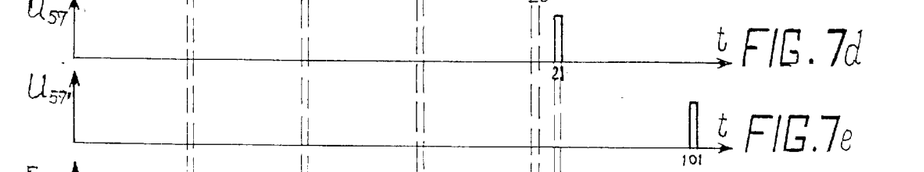
Figure 7F:
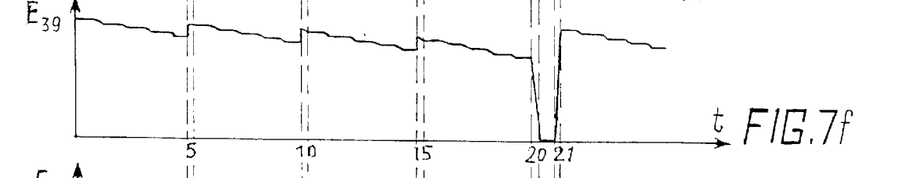
Figure 7G:
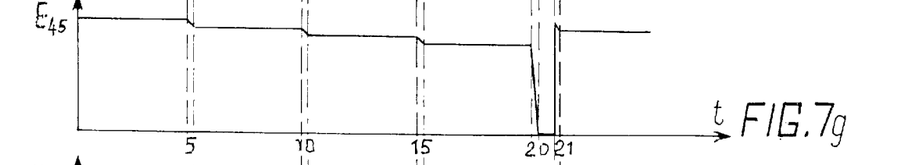
Figure 7H:
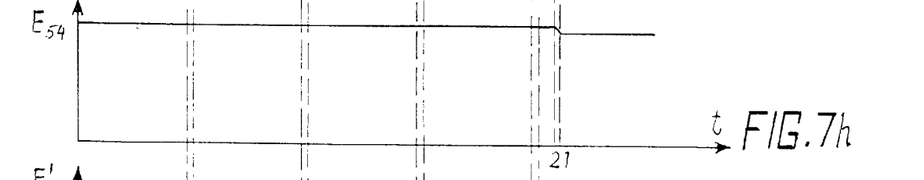
Figure 7I:
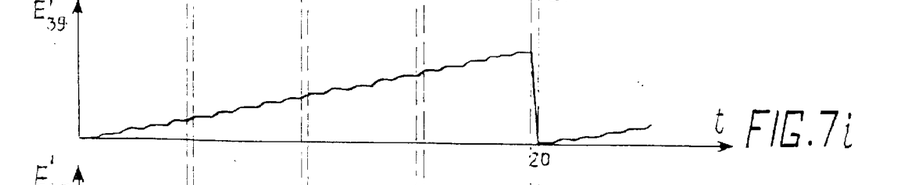
Figure 7J:
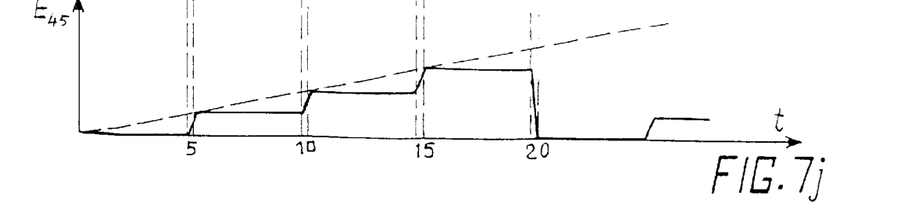
Figures 8A, 8B:
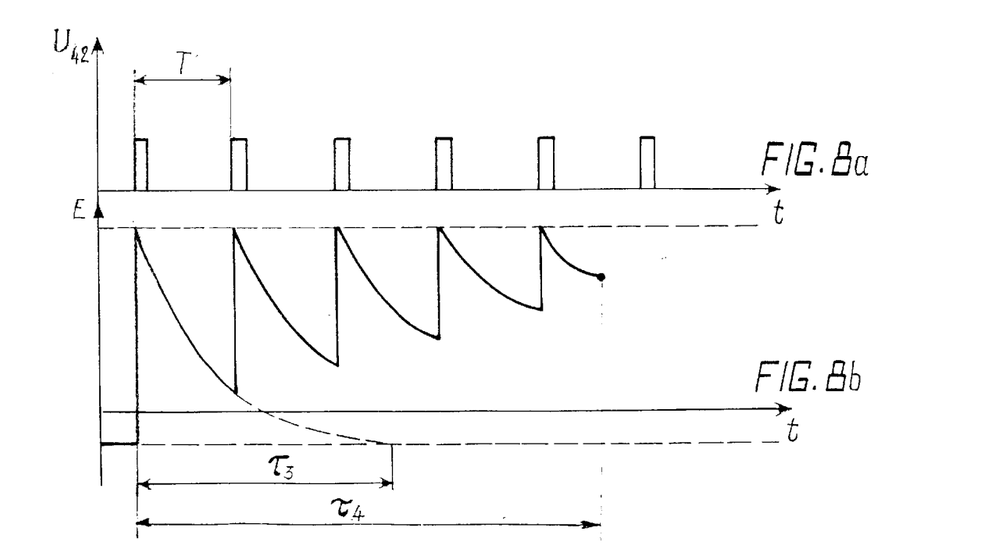

In the aforesaid device, collector junction 32 and emitter junction 33, which are respectively between the collector and base semiconductors 29, 30 and between the base and emitter semiconductors 30, 31, are used as the means 40 or 46 or 55 for changing temperature. These semiconductors are connected to a source 34 via a switch 35. The temperature T to which the crystalline semiconductors 29, 30, 31 are heated is determined by the power P which is dissipated on the semiconductor Junctions 32, 33 when current flows, and is determined by the equation $T=f(P)$, $P=I_1 \times U = I_2 \times \beta \times U$.

Using a current setting element 36 connected to the base semiconductor 30, it is possible to adjust the value of the current flowing through the base semiconductor 30, and consequently the temperature T to which the chip 28 is heated.

Crystals of silicon, germanium, diamond and gallium arsenide may be used as the crystalline semiconductor.

The method for changing the activity of a strain of pathogenic microorganisms is carried out in the following manner.

A device for changing the activity of a strain of pathogenic microorganisms, containing a working cell 37 (FIG. 4), is used, including a means 39 for recording and reproducing a spectrum of radiation of biological cells, on which polarized electromagnetic radiation of a strain of inactivated pathogenic microorganisms is recorded in accordance with method indicated above.

The device with the means 39 for recording and reproducing a spectrum of radiation of biological cells is positioned directly adjacent a vessel 72 with a strain 73 of pathogenic microorganisms it being desired that the activity of the strain be reduced similar to the strain 16 of pathogenic microorganisms.

At least one cycle of changing the temperature of the means 39 for recording and reproducing a spectrum of radiation of biological cells during a period of time of from 1 msec to 1000 sec in a range of from 10° C. to 400° C. is carried out.

In the variant being described, the cycle of changing temperature is carried out according to a linear law during 20 sec in the range of from 20° C. to 130° C. In the process of changing temperature, the means 39 for recording and reproducing a spectrum of radiation of a strain of pathogenic microorganisms radiates polarized electromagnetic radiation.

The aforesaid polarized electromagnetic radiation of the means 39 for recording and reproducing a spectrum of radiation of biological cells is used to irradiate the strain 73 of pathogenic microorganisms. Membrane and transmembrane molecules positioned on the plasmatic membrane of the strain 73 will intensively absorb this radiation. As a result of the absorption they will change their form and will have a conformation similar to the conformation of the membrane and transmembrane molecules positioned on the plasmatic membrane of the inactivated strain 16 of pathogenic microorganisms. Wherein a potential is established on the plasmatic membrane of the strain 73 of pathogenic microorganisms, which is close to the potential of the inactivated strain 16 of pathogenic microorganisms, i.e. the strain 73 transfers to an inactivated state Diagrams are shown in FIG. 6 which are diagrams of a change of the value of the cutoff voltage E on the plasmatic membrane in relation to the number n of test tubes 72 with the strains 73 of pathogenic microorganisms therein which are sequentially inactivated with the device.

In FIG. 6 are shown the moments 6.1, 6.2 and 6.3 of switching on the auxiliary cell 44, which makes it possible to increase the value of the cutoff voltage E and to inactivate a number of test tubes with strains 73 which is ten times greater than when only one working cell is used.

In order to ensure effective inactivation of the strain 73 of pathogenic microorganisms and to exclude the recording of information from that strain onto the means 39, 45 and 44' of the working cell 37 and the auxiliary cells 44 and 44' in the process of the cycle of changing their temperature, it is necessary that the cutoff potential $E_{16}$ on the plasmatic membrane of the inactivated strain 16 of pathogenic microorganisms by module exceeds the potential $E_{73}$ on the plasmatic membrane of the strain 73 of pathogenic microorganisms which is being inactivated.

$$[E_{16}]>[E_{73\cdot}]$$

In order to ensure the successive effective inactivation of a large number n of test tubes 72 with strains 73 of pathogenic microorganisms therein, it is necessary that the cutoff potential $E_{16}$ on the plasmatic membrane of the strain 16 of pathogenic microorganisms by module would substantially exceed the potential $E_{73}$ on the plasmatic membrane of the strain 16 of pathogenic microorganisms which is being inactivated $$[E_{16}]>>[E_{73}].$$

The method for eliminating a strain of pathogenic microorganisms from a human or animal organism is carried out in the following manner.

A device (FIG. 4) for changing the activity of a strain of pathogenic microorganisms is used. The device is placed directly adjacent to a patient 74 and at least one cycle of changing the temperature of a crystal on which polarized electromagnetic radiation of a strain of inactivated pathogenic microorganisms is recorded is implemented.

At least one cycle of irradiation of the patient 74 is implemented with polarized radiation for a length of time of from 1 msec to 1000 sec with from 1 to 48 sessions a day during a period of from 3 days to 2 months.

The introduction of the auxiliary cells 44, 44', etc. makes it possible to effectively, successively inactivate a large number of times a strain of pathogenic microorganisms which are in a patient's organism, and which is identical to the strain 16 of pathogenic microorganisms.

After 4–16 sessions of treatment, restoration of the level of polarized electromagnetic radiation on the working cell 37 of the device is implemented by forming a control pulse at the output 48 of the control unit 41 and carrying out a cycle of changing the temperature of the means 45 for recording and reproducing of the auxiliary cell 44.

The generator 64 for deletion and the standard cells 53, 53', 53" are used to exclude accumulation of the recording of parasitic information in the working and auxiliary cells, i.e. to exclude the accumulation of polarized electromagnetic radiation from other strains of pathogenic microorganisms which are in a highly active state in a human organism.

The standard cell 53 is turned on after 20–200 conducted sessions of treatment after deletion of the information on the working cell 37 and the auxiliary cells 47, 47' and is used for restoration of the level of polarized electromagnetic radiation on the working cell 37 and on the auxiliary cells 44, 44'.

FIG. 7 shows time diagrams of the operation of the device for one working cell, one auxiliary cell and two standard cells.

FIGS. 7*a* and 7*b* show respectively a sequence of control pulses applied to the input of the working cell 37 and to the input of the auxiliary cell 44.

FIG. 7*c* shows a deletion pulse formed by the generator 64 of deletion and applied to the inputs of the working cell 37 and the auxiliary cells 44, 44'.

FIGS. 7*d* and 7*e* show pulses applied to the inputs of the first and second standard cells respectively.

FIG. 7*f* shows a diagram of a change of the level of polarized electromagnetic radiation of the working cell 37.

FIG. 7*g* shows a diagram of a change of the level of polarized electromagnetic radiation of the auxiliary cell 44.

FIG. 7*h* shows a diagram of a change of the level of polarized electromagnetic radiation of the standard cell 53.

FIG. 7*i* shows a diagram of a change of the parasitic polarized radiation of the working cell 37.

FIG. 7*j* shows a diagram of a change of the parasitic polarized radiation of the auxiliary cell 44.

It is evident from the presented diagrams that connection of the working cell 37 takes place during each session of inactivation of a strain of pathogenic microorganisms, connection of the auxiliary cell 44—at each fifth session of inactivation, connection of the generator 64 for deletion—at each 20th session, connection of the standard cell 53 at each 21st session, connection of the second standard cell 53'—at each 101st session.

Such an algorithm of operation makes it possible to ensure a high level of inactivation of a strain of pathogenic microorganisms with a large number of sessions of inactivation.

Now consideration will be given to the operation of the device with a concrete example of a change of the activity of bacterial cells *Staphylococcus aureus* in a human organism.

At first a culture of deposited *Staphylococcus aureus* cells is taken and by any known method they are put into a lowly active state, which is characterized by a high positive potential on their plasmatic membrane, for example, by subjecting them to ultraviolet radiation which has bacteriostatic action.

Then the spectrum of radiation of inactivated *Staphylococcus aureus* cells is received and recorded by the method described above.

When there is a change of the temperature of the crystalline semiconductors of the means for recording and reproducing of the working, auxiliary and standard cells in the process of their intensive absorption of polarized photons radiated by conformed membrane and transmembrane molecules of the plasmatic membrane of inactivated *Staphylococcus aureus* cells, stable energetic states are created in the crystalline semiconductors, which are capable of radiating similar photons during repeated cycles of a change of temperature.

Then the device is positioned directly adjacent to a patient 74, in the organism of which there are identical *Staphylococcus aureus* biological cells which are in an active state.

The algorithm of operation of the device may be any and, for example, correspond to the algorithm shown in FIG. 7, wherein the period T (FIG. 8) between sessions of action is set on the basis of the time of restoration $\tau_3$ of the activity of pathogenic microbes in a patient's organism.

$$T<\tau_3$$

Maintaining the *Staphylococcus aureus* cells in an inactivated state for a lengthy period of time $\tau_4$ makes it possible to completely free the patient's organism from this pathogenic *Staphylococcus aureus* microorganism by eliminating them with the immune system of a human and pushing them out with other microorganisms included in the makeup of the patient's microflora.

For example, to completely free the patient's organism from *Staphylococcus aureus* during an acute inflammatory process, it is necessary to carry out 6–24 sessions a day for 10–14 days, in the case of a chronic process it is necessary to carry out 3–6 sessions a day for 8–30 days.

It is possible to successively or simultaneously record several strains of pathogenic microorganisms into the device for recording polarized electromagnetic radiation. For example, all the known pathogenic strains of the Staphylococcus genus may be recorded in the device for recording polarized electromagnetic radiation. Then use of the device for changing the activity of a strain of pathogenic microorganisms in which polarized electromagnetic radiation of all known inactivated strains of the Staphylococcus genus are recorded, makes it possible to inactivate and then eliminate any pathogenic strain of the Staphylococcus genus, which is in the organism of a human or animal.

The proposed device may implement the inactivation in the organism of a human or animal of not only bacteria, but also viruses, fungi, mycoplasma, prions, single-celled simples and their toxins, wherein the device and method for their inactivation and elimination are similar to that described above.

What is claimed is:

1. A method for recording polarized electromagnetic radiation of an inactivated strain of pathogenic microorganisms, comprising the following steps, acting on a strain of pathogenic microorganisms deposited in a vessel with an extreme agent selected from the group consisting of ultraviolet radiation with a wavelength within the limits of from 0.1 to 0.3 $\mu$m for a period of time $\tau$ of from 10 to 300 sec, viruses and toxic substances, and during the action converting said strain of pathogenic microorganisms from an active state to an inactivated state, wherein the potential on a cellular shell of the microorganism and the conformation of membrane and transmembrane molecules positioned on said shell change, placing said strain of inactivated pathogenic microorganisms directly adjacent to a means for recording and reproducing a spectrum of radiation of biological cells, carrying out at least one cycle of changing the temperature of said means for recording and reproducing a spectrum of radiation of biological cells within the range of from 10° C. to 400° C. and while the temperature on said means for recording and reproducing a spectrum of radiation of biological cells is changing, recording polarized electromagnetic radiation with a wavelength in the range of from 3 μm to 10 mm of the inactivated strain of pathogenic microorganisms, forming stable energetic states on said means for recording and reproducing a spectrum of radiation of biological cells, by means of which said means for recording and reproducing a spectrum of radiation of biological cells is capable of radiating similar polarized electromagnetic waves during subsequent cycles of changes of its temperature.

2. The method according to claim 1, wherein at least one crystal selected from the group consisting of silicon, germanium, diamond, gallium arsenide is used as said means for recording and reproducing a spectrum of radiation of biological cells.

3. The method according to claim 1, wherein a chip containing at least two crystalline semiconductors having different types of conductance and at least one semiconductor junction is used as said means for recording and reproducing a spectrum of radiation of biological cells.

4. The method according to claim 1, wherein simultaneously with the recording of polarized electromagnetic radiation of the strain of inactivated pathogenic microorganisms on said means for recording and reproducing a spectrum of radiation of biological cells, action is effected on said strain of pathogenic microorganisms with electromagnetic radiation in the range of from 10 Hz to $10^{14}$ Hz.

5. The method according to claim 1, wherein the change of the temperature of said means for recording and reproducing a spectrum of radiation of biological cells is effected according to a linear law.

6. The method according to claim 1, wherein the change of the temperature of said means for recording and reproducing a spectrum of radiation of biological cells is effected according to a nonlinear law.

7. A method for changing the activity of a strain of pathogenic microorganisms, comprising the following steps, using a means for recording and reproducing a spectrum of radiation of biological cells on which polarized electromagnetic radiation of a strain of inactivated pathogenic microorganisms is recorded in accordance with the method of claim 1, placing said means for recording and reproducing a spectrum of radiation of biological cells directly adjacent to said strain of pathogenic microorganisms, the activity of which it is desired be reduced, to be similar to an inactivated strain of pathogenic microorganisms, effecting at least one cycle of changing the temperature of said means for recording and reproducing a spectrum of radiation of biological cells for from 1 msec to 1000 sec in the range of from 10° C. to 400° C., as a result of which said means for recording and reproducing a spectrum of radiation of biological cells radiates polarized electromagnetic radiation, using said polarized electromagnetic radiation of said means for recording and reproducing a spectrum of radiation of biological cells to irradiate a strain of pathogenic microorganisms, converting said strain of pathogenic microorganisms from an active state to an inactivated state by said strain of pathogenic microorganisms absorbing the polarized electromagnetic radiation from said means for recording and reproducing a spectrums of radiation of biological cells.

8. A device for recording polarized electromagnetic radiation of an inactivated strain of pathogenic microorganisms comprising a working cell disposed in a vessel with a strain of inactivated pathogenic microorganisms and having a least one means for recording and reproducing a spectrum of radiation of biological cells and a means for changing temperature which is coupled to said means for recording and reproducing a spectrum of radiation of biological cells, a control unit connected to said means for changing temperature, at least one auxiliary cell for restoring the level of polarized electromagnetic radiation of said strain of inactivated pathogenic microorganisms in said working cell, also disposed in said vessel with said strain of inactivated pathogenic microorganisms, having at least one means for recording and reproducing a spectrum of radiation of biological cells, and a means for changing temperature which is coupled to said means for recording and reproducing a spectrum of radiation of biological cells, the auxiliary cell being connected via first and second inputs to respectively an output of said control unit and to an output of the second auxiliary cell, and via its output to an input of said working cell, wherein said working cell and said auxiliary cell are electrically coupled by means of a wire to each other and to said strain of inactivated pathogenic microorganisms.

9. The device according to claim 8, which additionally comprises at least one standard cell disposed in said vessel with the strain of inactivated pathogen microorganisms, serving for restoration of the level of polarized electromagnetic radiation of said strain of inactivated pathogenic microorganisms in said working cell and in said auxiliary cell, having at least one means for recording and reproducing a spectrum of radiation of biological cells and a means for changing temperature which is coupled to said means for recording and reproducing a spectrum of radiation of biological cells, and connected respectively via its inputs to an output of the control unit and to outputs of additional standard cells, and via its output to an input of said working cell and to inputs of the auxiliary cells, said standard cell is electrically coupled to said working cell, to said auxiliary cell and to said strain of inactivated pathogenic microorganisms by means of an electrical link.

10. The device according to claim 8, which additionally comprises a generator of electromagnetic oscillations which is mounted directly adjacent to said vessel containing said strain of inactivated pathogenic microorganisms.

11. The device according to claim 8, wherein a chip containing at least two crystalline semiconductors having different types of conductance and at least one semiconductor junction is used as said means for recording and reproducing a spectrum of radiation of biological cells.

12. The device according to claim 8, wherein at least one crystal selected from the group consisting of silicon, germanium, diamond, gallium arsenide is used as said means for recording and reproducing a spectrum of radiation of biological cells.

13. A device for changing the activity of a strain of pathogenic microorganisms comprising a working cell having a least one means for recording and reproducing a spectrum of radiation of biological cells on which polarized electromagnetic radiation of a strain of inactivated pathogenic microorganisms is recorded, and a means for changing of temperature which is coupled to said means for recording and reproducing a spectrum of radiation of biological cells, a control unit connected to said means for changing temperature, at least one auxiliary cell for restoring the level of polarized electromagnetic radiation of said strain of inactivated pathogenic microorganisms in said working cell, having at least one means for recording and reproducing a spectrum of radiation of biological cells on which polarized electromagnetic radiation of said strain of inactivated pathogenic microorganisms is recorded, and a means for changing temperature which is coupled to said means for recording and reproducing a spectrum of radiation of biological cells, the auxiliary cell being connected via first and second inputs to respectively an output of said control unit and to an output of the auxiliary cells, and via an output to an input of said working cell.

14. The device according to claim 13, which additionally comprises at least one standard cell serving for restoration of the level of polarized electromagnetic radiation of said strain of inactivated pathogenic microorganisms in said working cell and in said auxiliary cell, having at least one means for recording and reproducing a spectrum of radiation of biological cells on which polarized electromagnetic radiation of said strain of inactivated pathogenic microorganisms is recorded, and a means for changing temperature which is coupled to said means for recording and reproducing a spectrum of radiation of biological cells, and connected respectively via first and second inputs to an output of said control unit and to outputs of standard cells, and via its output to an input of said working cell and to inputs of the auxiliary cells, a unit for deleting polarized electromagnetic radiation, an input of which is connected to an output of said control unit, an output to an input of said working cell and to inputs of said auxiliary cells, and serving to delete polarized electromagnetic radiation from said working cell and said auxiliary cells.

15. The device according to claim 13, wherein said working cell, at least one said auxiliary cell and at least one said standard cell are positioned directly adjacent to each other and are coupled to each other by means of an electromagnetic link.

16. The device according to claim 13, wherein a chip containing at least two crystalline semiconductors having different types of conductance and at least one semiconductor junction is used as said means for recording and reproducing a spectrum of radiation of biological cells.

17. A method for eliminating a strain of pathogenic microorganisms from the organism of a human being or animal, comprising the following steps using the device for changing the activity of a strain of pathogenic microorganisms in accordance with claim 13, said device is disposed directly adjacent to the patient and at least one cycle of changing the temperature of the means for recording and reproducing a spectrum of radiation of biological cells, on which polarized electromagnetic radiation of an inactivated strain of pathogenic microorganisms is recorded, is carried out, at least one cycle of irradiation of a patient is carried out with polarized electromagnetic radiation having a length of from 1 msec to 1000 sec within a frequency within the limits of from 1 to 48 sessions per day for from 3 days to 2 months.

* * * * *

UNITED STATES PATENT AND TRADEMARK OFFICE
CERTIFICATE OF CORRECTION

PATENT NO. : 6,654,627 B2
DATED : November 25, 2003
INVENTOR(S) : Petrenko, Sergei Ivanovich It is certified that error appears in the above-identified patent and that said Letters Patent is hereby corrected as shown below:

<u>Title page,</u>
Item [56], References Cited, OTHER PUBLICATIONS, "Luminescene" should read
-- Luminescence --; and "N.L. Lupichev," reference "homepathy" should read
-- homeopathy --
Item [57], ABSTRACT,
Line 5, "a method" should read -- and a method --

<u>Column 3,</u>
Line 23, "Gurich" should read -- Gurwitsch --
Line 28, "Gurvich" should read -- Gurwitsch --
Line 29, "this" should read -- his --

<u>Column 5,</u>
Line 31, "¶means" should read -- means -- (i.e., append to previous line)

<u>Column 6,</u>
Line 17, "changing," should read -- changing --
Line 44, "¶in accordance" should read -- in accordance -- (i.e., append to previous line)

<u>Column 7,</u>
Line 36, "¶in accordance" should read -- in accordance -- (i.e., append to previous line)

<u>Column 10,</u>
Line 17, "19'!" should read -- 19' --
Line 67, "to" should be deleted

UNITED STATES PATENT AND TRADEMARK OFFICE
CERTIFICATE OF CORRECTION

PATENT NO. : 6,654,627 B2
DATED : November 25, 2003
INVENTOR(S) : Petrenko, Sergei Ivanovich It is certified that error appears in the above-identified patent and that said Letters Patent is hereby corrected as shown below:

<u>Column 16,</u>
Line 66, "time $\tau$" should read -- time t --

Signed and Sealed this

Thirteenth Day of April, 2004

JON W. DUDAS
*Acting Director of the United States Patent and Trademark Office*